United States Patent [19]

Tsai

[11] 4,210,447
[45] Jul. 1, 1980

[54] DENTAL RESTORATIONS USING CASTINGS OF NON-PRECIOUS METALS

[75] Inventor: Min H. Tsai, Van Nuys, Calif.

[73] Assignee: Unitek Corporation, Monrovia, Calif.

[21] Appl. No.: 962,118

[22] Filed: Nov. 20, 1978

Related U.S. Application Data

[63] Continuation-in-part of Ser. No. 854,407, Nov. 23, 1977, abandoned, which is a continuation-in-part of Ser. No. 743,192, Nov. 19, 1976, which is a continuation of Ser. No. 643,621, Dec. 23, 1975, which is a continuation of Ser. No. 465,837, May 1, 1974, abandoned.

[51] Int. Cl.$^2$ ............................................. C22C 19/05
[52] U.S. Cl. ......................................... 75/171; 427/2; 433/207
[58] Field of Search ............... 75/171; 427/2; 32/2, 8, 32/12

[56] References Cited

U.S. PATENT DOCUMENTS

| 3,160,500 | 12/1964 | Eiselstein et al. | 75/171 |
| 3,716,418 | 2/1973 | Kochavi | 148/6.3 |
| 3,761,728 | 9/1973 | Kochavi | 29/160.6 |
| 3,841,868 | 10/1974 | Dudek et al. | 75/171 |
| 3,843,359 | 10/1974 | Fiene et al. | 75/171 |
| 3,914,867 | 10/1975 | Manning et al. | 32/2 |
| 4,053,308 | 10/1977 | Tesk et al. | 75/171 |
| 4,118,223 | 10/1978 | Acuncius et al. | 75/171 |

OTHER PUBLICATIONS

Moon et al, "The Burnishability of Dental . . . Alloys" J. Prosthet. Dent, Oct. 1976, vol. 36, p. 404.

Primary Examiner—L. Dewayne Rutledge
Assistant Examiner—Upendra Roy
Attorney, Agent, or Firm—Christie, Parker & Hale

[57] ABSTRACT

A method and material for making dental restorations by using a porcelain-covered body of a non-precious metal alloy. The alloy preferably includes about 58–68% nickel, 18–23% chromium, 6–10% molybdenum, up to 5% of at least one rare-earth element, up to 4% columbium plus tantalum, up to 2% iron, and lesser quantities of carbon, aluminum, titanium, silicon and manganese. The alloy is resistant to corrosion by mouth fluids, is easy to finish and polish, and is closely matched to the thermal-expansion properties of commercially available dental porcelains. The alloy does not contaminate alloy-melting crucibles, exhibits excellent bonding characteristics to dental porcelains, is easy to melt and cast, and has sufficient ductility to enable margin burnishing of dental-restoration castings of the alloy.

3 Claims, No Drawings

DENTAL RESTORATIONS USING CASTINGS OF NON-PRECIOUS METALS

CROSS REFERENCES TO RELATED APPLICATIONS

This application is a continuation-in-part of copending application Ser. No. 854,407 filed Nov. 23, 1977 now abandoned, which was a continuation-in-part of application Ser. No. 743,192 filed Nov. 19, 1976, which was a continuation of application Ser. No. 643,621 filed Dec. 23, 1975, which was in turn a continuation of application Ser. No. 465,837 filed May 1, 1974 now abandoned.

BACKGROUND OF THE INVENTION

Dental restorations such as crowns or artificial teeth have traditionally been made by firing porcelain on a cast body of precious metal such as an alloy of gold. The physical properties of these precious alloys are well understood in dentistry, and the alloys bond properly with porcelain and are compatible for use in the mouth. Gold alloys are easy to melt and cast, are sufficiently ductile to permit burnishing of casting margins in the finishing of dental restorations, and can be polished to a high luster to resist plaque formation. Alloys of precious metals, however, are relatively heavy, and have increased in cost to such an extent that substitute materials have been sought in recent years.

It is now known that certain stainless alloys of non-precious metals can be used in dentistry, and examples of specific nickel alloys and processing techniques are set forth in U.S. Pat. Nos. 3,716,418, 3,727,299, 3,749,570 and 3,761,728, the disclosures of these patents being incorporated herein by reference. These nickel alloys have a higher modulus of elasticity than that of precious metal alloys, contributing to better sag resistance of the ceramo-metal structure after repeated firings in a furnace.

The higher strength of nickel alloys enables use of thinner castings which minimize reduction of the natural tooth structure in preparation for installation of the restoration. Nickel-alloy restorations are also light in weight and low in thermal conductivity, and these features provide greater comfort to a patient with a sensitive or deeply involved tooth. These alloys bond satisfactorily to porcelain, and further have the important economic advantage of being significantly lower in cast than gold or other precious-metal alloys.

There are various shortcomings of known nickel alloys. For example, these alloys are difficult to finish and polish, thereby requiring more dental laboratory time as compared to precious-metal alloys. Bond strengths of nickel alloys to dental porcelains are sensitive to the necessary repeated firings in laboratory manipulation and preparation, and this factor can affect clinical performance of the porcelain and nickel-alloy system. It is desirable, therefore, for a nickel alloy to have a high porcelain-metal bond strength to be compatible with the laboratory processing involved in making a restoration. Another problem is that slags of known nickel alloys tend to adhere to clay crucibles used to melt the alloy prior to casting. It takes time and effort to grind or chip off these tenacious slags to avoid possible contamination of other alloys during subsequent casting.

It is believed that these and other problems arise from the use in known alloys of elements such as beryllium, tin, silicon, gallium and boron which are added for improved melting and casting performance. In contrast to precious-alloy ingots which melt into a pool with little or no slag, prior-art nickel-alloy ingots tend to form into an individual molten mass covered by a thick slag when melted by a torch. This problem is at least partially controlled by use of the aforementioned elements, but not without incurring other problems.

For example, beryllium poses a health risk if not carefully handled during alloy processing. Alloys containing significant amounts of silicon and gallium tend to be brittle, and have an as-cast elongation of only about 2% due to the formation of intermetallic compounds. Alloys of this type must be heat treated at 1800° F. for about 30 minutes, followed by slow cooling in air, to provide sufficient ductility for margin burnishing, and the increased labor cost arising from this processing tends to cancel the reduced cost of a nonprecious alloy. Some other alloys exhibit satisfactory ductility (over 5% elongation as cast), but microscopic carbides and intermetallics in the alloy result in more difficult and time-consuming shaping and polishing as compared to castings of precious alloys.

The new alloy of this invention overcomes these disadvantages of known nickel alloys, while maintaining the advantages of these materials as described above.

SUMMARY OF THE INVENTION

This invention relates to the use of non-precious alloys characterized by high nickel-chrome content, and by the inclusion of molybdenum, columbium plus tantalum, at least one element selected from the rare-earth family, and other lesser components to provide thermal-expansion characteristics closely matched to commercially available dental porcelains, excellent bonding characteristics to these porcelains, good ductility, and easy shaping and polishing characteristics.

DESCRIPTION OF THE PREFERRED EMBODIMENT

The non-precious dental alloy of this invention has the following elemental components (percentages are by weight):

| Element | Acceptable Range (%) |
| --- | --- |
| Nickel | 58–68 |
| Chromium | 18–23 |
| Molybdenum | 6–10 |
| Columbium plus tantalum | 0.1–4 |
| One or more rare-earth elements | 0.01–5 |
| Iron | 0.20–2 |
| Silicon | 0.01–0.5 |
| Manganese | 0.01–0.4 |
| Titanium | 0.01–0.2 |
| Aluminum | 0.01–1.0 |
| Carbon | 0.01–0.1 |

The relatively high chromium content of the alloy, and the use of molybdenum, provide satisfactory corrosion resistance when the alloy is exposed to mouth fluids. The ranges specified for other elemental components are important to insure proper formation of carbide in the alloy (tantalum, columbium, titanium and chromium), for precipitation of the gamma-prime phase (aluminum and titanium), and for solid-solution hardening (molybedenum), these factors all contributing to strength and desired ductility of the final cast alloy. Nickel, chromium and molybdenum are the primary determinants of the thermal-expansion properties of the alloy, though the other components play some role in this characteristic. One or more rare-earth elements (defined as those elements with atomic numbers from 57 through 71 in the periodic chart of elements) and the use of aluminum, contribute to the ease of shaping and polishing the alloy, and provide good melting and casting characteristics. Beryllium and tin are avoided in formulating the alloy.

The components are alloyed by induction melting under argon, and rare-earth elements are the last addition to the melt. The molten alloy is cast into small slugs or pellets for convenient remelting when the alloy is subsequently cast into a dental prosthesis.

Conventional techniques are used to make a finished dental restoration with the alloy. A ceramic mold is prepared using the usual lost-wax or burnout-plastic methods. The alloy is then melted (a torch fed with propane at 10 psi and oxygen at 20 psi is used to achieve a 2360°–2450° F. melting range of the alloy) and poured in the mold which is mounted in a centrifugal casting machine. After cooling, the mold is broken away and the casting is cleaned, trimmed, polished and finished in preparation for application of porcelain by the usual firing techniques.

Polishing of the alloy is done with conventional equipment such as a Shofu Brownie and Greenie rubber wheel. The casting is brought to a high luster with an Abbott-Robinson brush (used with polishing compound) and Black's felt wheels impregnated with tin oxide.

The alloys of this invention are particularly well matched to the thermal properties of commercially available dental porcelains such as distributed by Vita Zahnfabrik under the trademark VMK-68, distributed by Dentsply International, Inc. under the trademark BIOBOND and those distributed by Ceramco Division of Johnson & Johnson. These above-named dental porcelains generally form a strong bond to the metal alloy casting of the present invention.

The alloys are also useful in making removable dental appliances such as orthodontic retainers. The relative softness of the alloys avoids surface damage to natural teeth over which the appliance is fitted, and the alloys are sufficiently ductile to permit hand shaping for interim of final alignment of the appliance. Utility of the invention is thus not limited to appliances on which porcelain is fired.

Strength, elongation and modulus of elasticity are tested by using an Instron tensile instrument. Vickers hardness is obtained by testing specimens of the alloy with a microhardness tester with diamond indenter. Thermal expansion coefficients are measured with a dilatometer. These tests and instruments are well known to those skilled in the art.

Typical properties of the alloy of this invention as cast are as follows:
  Ultimate tensile strength: 75,000 psi
  Yield strength (0.2% offset): 54,000 psi
  Modulus of elasticity: $27 \times 10^6$ psi
  Elongation: 8 percent
  Vickers hardness: 200
  Thermal expansion coefficient: $14 \times 10^{-6}$°C.$^{-1}$ The following examples further illustrate the invention and some of the tests which have been made in evaluating the invention, and are not intended to be limiting. The figures shown are element percentages by weight.

| | Example 1 | Example 2 | Example 3 |
|---|---|---|---|
| Nickel | 63.06 | 60.54 | 62.80 |
| Chromium | 21.60 | 20.74 | 21.76 |
| Molybdenum | 8.40 | 8.06 | 8.45 |
| Dysprosium | 1.00 | 5.00 | 0 |
| Neodymium | 0 | 0 | 1.00 |
| Columbium plus Tantalum | 3.80 | 3.64 | 3.85 |
| Iron | 1.25 | 1.20 | 1.25 |
| Silicon | 0.35 | 0.33 | 0.34 |
| Manganese | 0.28 | 0.27 | 0.27 |
| Aluminum | 0.10 | 0.10 | 0.12 |
| Titanium | 0.10 | 0.07 | 0.10 |
| Carbon | 0.06 | 0.05 | 0.06 |

Alloys of Examples 1 through 3 melt similarly to precious alloys, and form only very thin layers of oxide which cover the molten alloy pool. These alloys are easy to shape and to polish, and exhibit good ductility for burnishing the margins of castings.

| | Example 4 | Example 5 | Example 6 |
|---|---|---|---|
| Nickel | 60.62 | 62.37 | 64.18 |
| Chromium | 21.12 | 20.87 | 21.22 |
| Molybdenum | 8.12 | 8.26 | 8.34 |
| Samarium | 5.00 | 0 | 0 |
| Praseodymium | 0 | 3.00 | 0 |
| Gadolinium | 0 | 0 | 0.50 |
| Columbium plus Tantalum | 3.11 | 3.42 | 3.71 |
| Iron | 1.23 | 1.24 | 1.20 |
| Silicon | 0.32 | 0.32 | 0.30 |
| Manganese | 0.25 | 0.28 | 0.29 |
| Aluminum | 0.10 | 0.11 | 0.13 |
| Titanium | 0.08 | 0.07 | 0.09 |
| Carbon | 0.05 | 0.06 | 0.04 |

Alloys of these examples are melted easily and are ductile. These alloys are not shaped and polished as easily as alloys of Examples 1 through 3.

| | Example 7 | Example 8 | Example 9 |
|---|---|---|---|
| Nickel | 60.01 | 62.99 | 62.46 |
| Chromium | 21.00 | 21.60 | 21.63 |
| Molybdenum | 8.20 | 8.40 | 8.40 |
| Cerium | 2.50 | 0.50 | 0.50 |
| Lanthanum | 1.50 | 0.50 | 0.50 |
| Neodymium | 0.70 | 0 | 0 |
| Praseodymium | 0.30 | 0 | 0 |
| Tin | 0 | 0 | 0.60 |
| Columbium plus Tantalum | 3.72 | 3.80 | 3.80 |
| Iron | 1.23 | 1.25 | 1.25 |
| Silicon | 0.32 | 0.35 | 0.35 |
| Manganese | 0.26 | 0.28 | 0.28 |
| Aluminum | 0.12 | 0.17 | 0.07 |
| Titanium | 0.09 | 0.10 | 0.10 |
| Carbon | 0.05 | 0.06 | 0.06 |

Alloys of Example 7 through 9 are ductile. Alloys of Example 7 and 8 are very easy to shape and polish. The alloy of Example 9 which contains tin is difficult to shape and polish. Alloys of Example 7 through 9 when melted form a molten mass covered by a somewhat thicker oxide as compared to alloys of Example 1 through 3.

What is claimed is:

1. A non-precious metal base for a dental restoration, comprising:
   a body of a stainless metal alloy configured for intra-oral installation, the alloy comprising about:
   58 to 68 percent nickel, 18 to 23 percent chromium, 6 to 10 percent molybdenum, 1 to 4 percent columbium plus tantalum, and 0.01 to 5 percent of at least one rare-earth element selected from the group consisting of lanthanum, cerium, praseodymium, neodymium, samarium, gadolinium, and dysprosium.

2. A dental restoration, comprising:
   a body of stainless metal alloy configured for intra-oral installation, and a porcelain jacket fired on the alloy body, the alloy comprising:
   nickel, 58 to 68 percent;
   chromium, 18 to 23 percent;
   molybdenum, 6 to 10 percent;
   columbium plus tantalum, 1 to 4 percent;
   iron, 0.02 to 2 percent;
   silicon, 0.01 to 0.5 percent;
   manganese, 0.01 to 0.4 percent;
   titanium, 0.01 to 0.2 percent;
   aluminum, 0.01 to 1.0 percent;
   carbon, 0.01 to 0.1 percent; and
   0.01 to 5 percent of at least one rare-earth element selected from the group consisting of lanthanum, cerium, praseodymium, neodymium, samarium, gadolinium, and desprosium.

3. A method for making a dental restoration, comprising: firing a porcelain jacket on a body of non-precious metal alloy, the alloy comprising:
   nickel, 58 to 68 percent;
   chromium, 18 to 23 percent;
   molybdenum, 6 to 10 percent;
   columbium plus tantalum, 1 to 4 percent;
   iron, 0.02 to 2 percent;
   silicon, 0.01 to 0.5 percent;
   manganese, 0.01 to 0.4 percent;
   titanium, 0.01 to 0.2 percent;
   aluminum, 0.01 to 1.0 percent;
   carbon, 0.01 to 0.1 percent; and
   0.01 to 5 percent of at least one rare-earth element selected from the group consisting of lanthanum, cerium, praseodymium, neodymium, samarium, gadolinium, and dysprosium.

* * * * *